US00PP36170P2

(12) United States Plant Patent
Meilland

(10) Patent No.: US PP36,170 P2
(45) Date of Patent: Oct. 1, 2024

(54) BEDDING ROSE PLANT NAMED 'MEILLERSROC'

(50) Latin Name: *Rosa hybrida*
Varietal Denomination: MEILLERSROC

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/233,017

(22) Filed: Aug. 11, 2023

(51) Int. Cl.
*A01H 5/02* (2018.01)
*A01H 6/74* (2018.01)

(52) U.S. Cl.
USPC ..... Plt./108
CPC ..... *A01H 6/749* (2018.05); *A01H 5/02* (2013.01)

(58) Field of Classification Search
USPC ..... Plt./101, 102, 108
See application file for complete search history.

(56) References Cited

U.S. PATENT DOCUMENTS

PP21,709 P2 2/2011 Carruth

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of bedding rose plant, referred to by its cultivar name, 'MEILLERSROC', is disclosed. The new variety forms attractive, double, red colored flowers. Attractive dense, glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida*.

Variety denomination: 'MEILLERSROC'.

STATEMENT REGARDING PRIOR DISCLOSURES BY THE INVENTOR

The first offer for sale of the new variety was Oct. 7, 2022, in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was the 'MEIPAONIA' variety (not patented). The male parent (i.e., the pollen parent) of the new variety was an unnamed seedling (not patented) which is the product of a cross between the 'NOAWEL' variety (not patented) and the 'MEICOLOSS' variety (not patented).

The parentage of the new variety can be summarized as follows:

'MEIPAONIA' X ('NOAWEL' X 'MEICOLOSS')

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) produces red colored flowers,
(b) displays a bushy growth habit, and
(c) emits a slight spicy, cinnamon fragrance.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'MEIPAONIA' variety (i.e., the seed parent) produces yellow flowers with pink tones, whereas the new variety produces red colored flowers. In addition, the unnamed seedling male parent (i.e., pollen parent) is a bigger and larger plant compared to the new variety. Moreover, the new variety can be readily distinguished from other similar non-parental varieties. For example, the 'WEKcobeju' variety (U.S. Plant Pat. No. 21,709) provides flowers with a lower number of petals (about 16 to 24 petals) that emit a fruity fragrance compared to the new variety, which provides flowers that have typically between 30 to 40 petals and emit a light spicy and cinnamon fragrance.

The new variety has been named 'MEILLERSROC'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately three years of age and were observed during May while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of three-years-old specimens of the new variety during May while budded on their own roots and growing outdoors at Le Cannet des Maures, Var, France.

Botanical classification: *Rosa hybrida* cultivar MEILLERSROC.

Commercial classification: Bedding Rose Plant.

Plant:

*Habit*.—Bushy.

*Height*.—Approximately 50 cm on average.

*Width*.—Approximately 50 cm on average.

Branches:

*Color*.—Young stems: Commonly near Yellow-Green Group 144A sometimes suffused with near Greyed-Purple Group 184A. — adult wood: commonly near Green Group 143C.

*Length*.—From the crown to the flower is approximately 40 cm on average.

*Diameter*.—Typically between 0.4 cm to 0.5 cm.

*Thorns*.—Configuration on adult stems: Very concave, elongated and curved downwards on the upper surface and very concave on the under surface. — long prickles—quantity: approximately 9 thorns on average per 10 cm long young stem and approximately 20 thorns on average per 10 cm long adult stem. — long prickles—length: approximately 0.5 cm on average on young stems and on adult stems. — long prickles—width at base: typically between 0.1 cm to 0.2 cm on young stems and on adult stems. — long prickles—base shape: elliptical, broad, and short on young and adult stems. — long prickles—color on young stems: commonly near Yellow-Green Group 145A amply suffused with near Greyed-Purple Group 185B. — long prickles—color on adult stems: commonly near a color between Greyed-Orange Group 166A and 166B. — small prickles: absent.

*Internode*.—Numbers on the entire branch: Typically between 4 to 7. — length: typically between 1.5 cm to 3.0 cm.

Foliage:

*General appearance*.—Dense, glossy.

*Number of leaflets*.—3, 5; most often 5.

5 *leaflets leaf*.—Length: approximately 8.0 cm on average. — width: approximately 5.5 cm on average.

*Terminal leaflet*.—Length: approximately 3.0 cm on average. — width: approximately 2.5 cm on average.

*Young shoots*.—Anthocyanin coloration: slight and commonly near Greyed-Purple Group 187B.

*New foliage*.—Upper surface color: commonly near a color between Green Group 139A and Green Group 137A. — under surface color: commonly near Green Group 137C.

*Adult foliage*.—Upper surface color: commonly near a color between Green Group 139A and Green Group 141A. — under surface color: commonly near Green Group 137C.

Leaflets:

*Shape*.—Tip: acuminate. — base: obtuse.

*Intensity of glossiness*.—Strong.

*Texture*.—Moderately leathery.

*Smoothness*.—Upper and under surfaces are smooth.

*General appearance*.—Elliptical.

*Serration*.—Small and single.

*Undulation on the margin*.—Strong.

*Venation*.—Color is commonly near Yellow-Green Group 144B and pattern is imparipinnate.

*Petiole rachis*.—Color of upper surface: commonly near Yellow-Green Group 144A on the edges and near Yellow-Green Group 144B in the middle, and sometimes slightly suffused with near Greyed-Purple Group 183B. — color of under surface: commonly near Yellow-Green Group 144B. — texture: upper surface is glandular, under surface is small prickles. — rachis of terminal leaflet: length is typically between 2.0 cm to 2.5 cm and diameter is approximately 0.1 cm on average.

*Petioles*.—Upper surface: glandular. — under surface: small prickles. — color of upper surface: commonly near Yellow-Green Group 144A on the edges and near Yellow-Green Group 144B in the middle, and sometimes slightly suffused with near Greyed-Purple Group 183B. — color of under surface: commonly near Yellow-Green Group 144B. — length: typically between 2.0 cm to 3.0 cm. — diameter: approximately 0.1 cm on average.

*Stipules*.—Length: approximately 1.5 cm on average. — width: approximately 0.6 cm on average. — general appearance: broad. — texture: smooth on upper and under surfaces. — color of upper surface: commonly near Green Group 143B suffused with near Green Group 143A. — color of under surface: commonly near Green Group 143C suffused with near Green Group 143B.

Inflorescence:

*Number of flowers per stem*.—Typically between 1 to 3 flowers per stem.

*Lastingness of the bloom*.—On the plant: approximately 7 days. — in vase: not tested.

*Bud*.—Shape: ovoid. — size: medium. — length: typically between 2.0 cm to 2.5 cm. — width: approximately 1.5 cm on average. — color as calyx breaks: upper surface: commonly near Red Group 43B amply suffused with near Red-Purple Group 60A; basal spot is commonly near Yellow Group 5C. under surface: commonly near Red Group 46D; basal is commonly near Yellow Group 8D.

*Sepals*.—Number: commonly 5. — length: approximately 2.0 cm on average. — width: approximately 0.6 cm on average. — shape: at the top: elongated and narrow. at the base: flat at union with the receptacle. — extensions: typically 2 sepals without extensions, 3 sepals with weak extension. — upper surface: texture: tomentous. color: commonly near Yellow-Green Group 144B at the base entirely covered with near Greyed-Purple Group 187B going towards the apex and covered with many hairs near White Group 155B. — under surface: texture: glandular on the edges. color: commonly near Yellow-Green Group 144B at the base entirely covered with near Greyed-Purple Group 187B going towards the apex.

*Receptacle*.—Color: commonly near Yellow-Green Group 144A sometimes slightly suffused with near Greyed-Purple Group 187B. — length: approximately 0.6 cm on average. — width: approximately 0.6 cm on average. — surface: smooth. — shape: pitcher shaped.

*Peduncle*.—Length: typically between 2.0 cm to 3.0 cm. — width: approximately 0.2 cm on average. — surface: smooth. — color: commonly near Yellow-Green Group 144A amply suffused with near Greyed-Purple Group 187B.

*Flower*.—Diameter when open: typically 6.0 cm to 8.0 cm. — depth of the flower: approximately 2.0 cm on average. — shape: flat cup shaped. — shape when viewed from above: irregular rounded. — shape of the upper part of the flower profile: flat convex. — shape of the lower part of the flower profile: flat. — type: double. — number of petals under normal conditions: typically between 30 to 40. — petals: general shape: obovate rounded. shape at the base: acute. shape at the top: rounded. texture: soft. length: typically between 2.5 cm to 3.5 cm. width: typically between 2.0 cm to 3.0 cm. — undulation of the petal: medium. — reflexing of the petal: absent. — petal incision: medium. — petal arrangement: imbricated with few petaloids (crumpled little petal shape). — petal drop: petals drop off cleanly before drying. — fragrance: light spicy and cinnamon. — discoloration of the flower: light blueing. — color when opening: basal spot on the upper surface: commonly near Yellow Group 3C. upper surface: commonly near Red Group 43C amply suffused with near Greyed-Purple Group 186B. basal spot on the under surface: commonly near Yellow Group 8D. under surface: commonly near Red Group 52B. — color of the open flower: basal spot on upper surface: commonly near Yellow Group 8D. upper surface: commonly near Red Group 43C amply suffused with near Greyed-Purple Group 186C. basal spot on under surface: commonly near Yellow Group 8D. under surface of the flower: commonly near Red Group 52C. — anthers: typically between 90 to 100, length is approximately 0.2 cm on average, width is approximately 0.1 cm on average, coloration is commonly near Yellow-Orange Group 18B in the middle and near Yellow-Orange Group 23A on the edges, and arrangement is regular around styles. — filaments: length is typically between 0.3 cm to 0.6 cm and coloration is commonly near Yellow Group 3B at the base evolving towards near Red Group 39A towards the anther. — styles: length is typically between 0.5 cm to 0.7 cm, coloration is commonly near Green-White Group 157A at the base and near Red-Purple Group 57A near the stigma, and number is typically between 30 to 35. — stigmas: length is typically less than 0.1 cm and coloration is commonly near Yellow Group 3C. — pollen: very abundant quantity; color is commonly near Orange Group 24A. — hips: information not available.

Development:

*Vegetation*.—Strong.

*Blooming*.—Early in the season abundant and intermittent, typically from May to October in France.

*USDA hardiness zone*.—Zone 8 to 10.

*Tolerance to disease*.—Good, and particularly against downy mildew (*Peranospora sparsa*).

The new 'MEILLERSROC' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEILLERSROC' characterized by the following combination of characteristics:

(a) produces red colored flowers, (b) displays a bushy growth habit, and (c) emits a slight spicy, cinnamon fragrance;

substantially as herein shown and described.

* * * * *

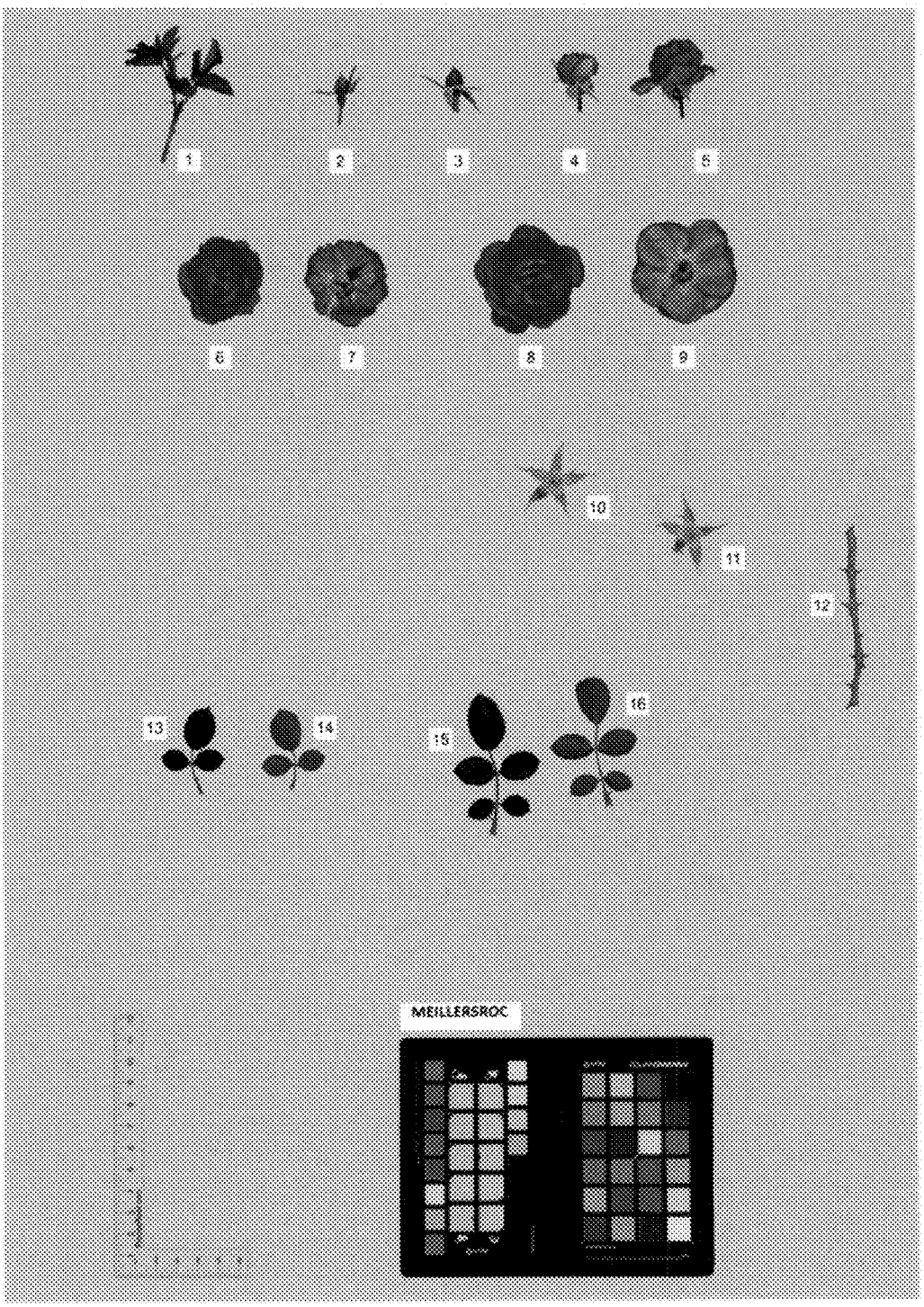
1
2
3
4
5
6
7
8
9
10
11
12
13
14
15
16
MEILLERSROC